United States Patent [19]

Magin

[11] Patent Number: 6,070,099
[45] Date of Patent: May 30, 2000

[54] DEFIBRILLATOR WITH IMPROVED UTILIZATION OF THE ACCUMULATOR ENERGY

[75] Inventor: Thomas Magin, Umkirch, Germany

[73] Assignee: Marquette Medical GmbH, Freiburg, Germany

[21] Appl. No.: 09/185,466

[22] Filed: Nov. 3, 1998

[30] Foreign Application Priority Data

Nov. 14, 1997 [DE] Germany .............................. 197 50 634

[51] Int. Cl.[7] ............................................... A61N 1/00
[52] U.S. Cl. ............................................. 607/5; 607/29
[58] Field of Search ...................... 607/5, 4, 29

[56] References Cited

U.S. PATENT DOCUMENTS

| | | | |
|---|---|---|---|
| 4,548,209 | 10/1985 | Wielders et al. | 128/419 D |
| 5,031,616 | 7/1991 | Mann et al. | 128/419 |
| 5,265,588 | 11/1993 | Nelson et al. | 607/5 |
| 5,447,522 | 9/1995 | Chang et al. | 607/7 |
| 5,488,553 | 1/1996 | Renger | 363/21 |
| 5,609,618 | 3/1997 | Archer | 607/74 |
| 5,700,280 | 12/1997 | Silvian | 607/5 |
| 5,741,307 | 4/1998 | Kroll | 607/5 |
| 5,773,961 | 6/1998 | Cameron et al. | 320/132 |
| 5,869,970 | 2/1999 | Palm et al. | 607/28 |
| 5,925,068 | 7/1999 | Kroll | 607/29 |

FOREIGN PATENT DOCUMENTS

| | | | |
|---|---|---|---|
| 0 598 225 A2 | 5/1994 | European Pat. Off. | A61N 1/39 |
| 31 11 116 A1 | 1/1982 | Germany | G01R 31/36 |
| 2 265 312 | 9/1993 | United Kingdom | A61N 1/38 |
| WO 95/11058 | 4/1995 | WIPO | A61N 1/39 |

*Primary Examiner*—Kennedy J. Schaetzle
*Attorney, Agent, or Firm*—Michael Best & Friedrich; Christian G. Cabou; Phyllis Y. Price

[57] ABSTRACT

The invention relates to a defibrillator having a capacitor (4) which is chargeable via a DC-DC converter (3) by an accumulator (i.e., rechargeable battery) (1). Between the accumulator (1) and the capacitor (4) there is situated a control device (2) which, as the internal resistance (Ri) of the accumulator (1) increases, draws a lower current from the latter, so that the output voltage of the accumulator (1) is kept approximately constant. Before the defibrillator is automatically deactivated and energy already stored in the capacitor is internally destroyed, the controller interrupts the charging of the capacitor when the residual energy remaining in the accumulator is less than an amount required to charge the capacitor to the desired energy.

7 Claims, 1 Drawing Sheet

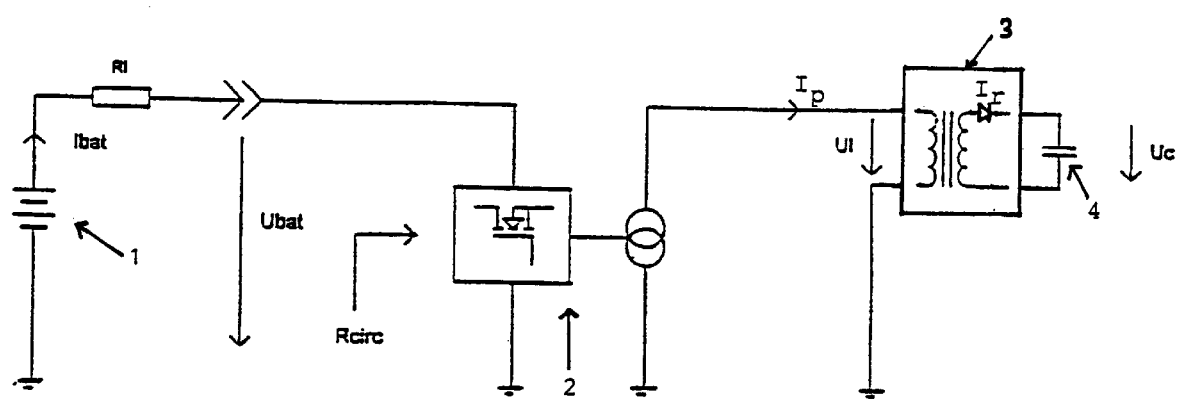

DEFIBRILLATOR WITH IMPROVED UTILIZATION OF THE ACCUMULATOR ENERGY

DESCRIPTION

The present invention relates to a defibrillator having a capacitor which is chargeable via a direct current/direct current converter by an accumulator, i.e., a rechargeable battery.

As is known in the case of cardiac arrhythmias, defibrillators are able to emit electrical current pulses having an energy of 2 to 500 J and a duration of approximately 4 to 8 ms to the body of a patient. In this case, so-called external or transthoracic defibrillators are portable systems which procure their energy from an accumulator. As a consequence of their portability, these defibrillators must not have an excessive weight; this in turn means the accumulators which are built into the defibrillators have only a limited capacity.

The current pulse to be emitted to the body of the patient is generated by the discharge of a capacitor which has previously been charged by the accumulator with interposition of a direct current/direct current (DC-DC) converter. As the energy of the accumulator decreases, its output voltage now falls during the charging of the capacitor finally to such an extent that the residual energy in the accumulator cannot be utilized any longer, since the defibrillator is deactivated beforehand.

Moreover, the electrical energy which is already stored in the capacitor of the defibrillator is internally destroyed in the defibrillator without emission of a current pulse to the patient, because this is stipulated to be so by safety regulations: no residual energy must remain in the capacitor after the elapse of a specified time, because this represents a hazard.

In addition, at the present time defibrillators are constructed in such a way that an operator, i.e. a physician or paramedic, sets the desired energy on the defibrillator. When the capacitor of the defibrillator has been charged to this energy, then the defibrillator reports this by means of an optical/acoustic signal and the operator can release the current pulse through the body of the patient. However, if this set energy cannot be reached, as a consequence of a decreasing accumulator energy, then after some time, as a consequence of the mentioned safety regulations, the energy stored in the capacitor of the defibrillator is internally destroyed.

In practice, it is now extremely unsatisfactory if, as a consequence of an accumulator energy coming to an end, the capacitor of a defibrillator can no longer be charged to the desired energy, since the residual energy still contained in the accumulator cannot be utilized. The same applies to a capacitor which has not been fully charged to the desired energy. Certainly, it is in many cases better for example to emit only 90% of the desired energy from a defibrillator to a patient than completely to relinquish a defibrillation or to apply the latter only after a relatively long period of time after equipping the defibrillator with a fully charged accumulator.

Accordingly, it is the object of the present invention to provide a defibrillator which is capable of utilizing the residual energy of an accumulator in optimal fashion.

In the case of a defibrillator of the initially mentioned type, this object is achieved according to the invention by a control device which is situated between the accumulator and the capacitor and which, as the internal resistance of the accumulator increases, draws a lower current from the latter, so that the output voltage of the accumulator is kept approximately constant.

In order to be able in all circumstances to utilize the energy already stored in the capacitor, in a further development of the invention it is provided that the control device interrupts the charging of the capacitor before the defibrillator is automatically deactivated and internally destroys the already stored energy, when the residual energy remaining in the accumulator is not sufficient to charge the capacitor to the desired energy, and that, moreover, the energy already stored in the capacitor is indicated.

In the text which follows, the invention is explained in greater detail with reference to the drawing, in the single figure of which a schematic block diagram of the defibrillator according to the invention is shown.

The figure shows an accumulator 1 having an internal resistance Ri, a control device consisting of a controlled current source 2, a DC-DC converter 3 and a capacitor 4.

In the case of constant-current charging of the capacitor 4, the following interrelationships have to be taken into consideration:

If the secondary current Is of the DC-DC converter 3 for the charging of the capacitor is kept constant, the voltage Uc at the capacitor 4 increases in proportion to the lapsed charging time t. Since the power P to be transferred through the DC-DC converter 3 is obtained from the product of the capacitor voltage Uc and the secondary current Is, this power P likewise increases in proportion to the lapsed charging time t.

As is known, the primary current Ip of the transformer included in the DC-DC converter 3 is directly proportional to the secondary current Is. In corresponding fashion, both currents Ip and Is are constant. Accordingly, the driving voltage U1 on the primary side of the transformer must likewise increase in proportion to the lapsed charging time t.

The power drawn from the constant current source 2 corresponds, to a first approximation, to the transferred power P; accordingly, it is proportional to the lapsed charging time t.

For the voltage supply from the accumulator 1, a constant voltage source can, to a first approximation, be assumed, the internal resistance of which is Ri as compared with the circuit resistance Rcirc. If a power increasing with the charging period is now drawn from the accumulator 1, then this leads to a likewise increasing accumulator current $I_{bat}$, since, as was presupposed, the terminal voltage $U_{bat}$ of the accumulator 1 remains constant.

It accordingly emerges that the accumulator current $I_{bat}$ is, to a first approximation, proportional to the lapsed charging time t of the capacitor 4.

If the energy stored in the accumulator 1 now decreases, then it is no longer possible to assume a constant internal resistance Ri. Rather, the internal resistance Ri of the accumulator 1 increases as the energy thereof decreases. In conjunction with the increasing accumulator current $I_{bat}$, this leads to a voltage drop across the internal resistance Ri during the charging phase, which voltage drop cannot be disregarded.

If, however, in the case of defibrillators to date, the accumulator voltage $U_{bat}$ decreases below a critical value, the defibrillator is automatically deactivated, and the energy already stored in the capacitor 4 is internally destroyed.

Use of the defibrillator is then possible only in circumstances in which the accumulator 1 is replaced by another accumulator which is sufficiently charged. This requires at least a duration of 20 seconds; this may frequently be extremely critical for a patient.

The automatic deactivation of the defibrillator can be prevented if, as the internal resistance Ri of the accumulator 1 increases, a lower current is drawn from the latter. In this way, the voltage drop across the internal resistance Ri can then be kept constant; this in turn leads to a constant accumulator voltage or terminal voltage $U_{bat}$.

In the case of the defibrillator according to the invention, use is made of the fact that an increasing internal resistance Ri of the accumulator 1 is made noticeable by a decreasing accumulator voltage $U_{bat}$: accordingly, the accumulator voltage $U_{bat}$ is monitored. Proceeding from a nominal value $U_{bat}$ for which the maximum current can be drawn from the accumulator 1, the accumulator current $I_{bat}$ is automatically readjusted in such a way that the accumulator voltage $U_{bat}$ falls only to such an extent that a further operation of the defibrillator is guaranteed.

In the case of the defibrillator according to the invention, the terminal voltage $U_{bat}$ of the accumulator is accordingly monitored. Proceeding from the recorded value for the terminal voltage, the accumulator current is readjusted in such a way that the terminal voltage $U_{bat}$ falls only to such an extent that charging of the capacitor 4 is still possible.

As a result of this, the charging time t of the capacitor 4 is indeed extended. However, it is possible to draw residual energy from an almost discharged accumulator.

Naturally, such a procedure is possible only within the limits of the residual energy remaining in the accumulator 1. Thus, should the residual energy remaining in the accumulator 1 no longer be sufficient to charge the capacitor 4 fully to the selected energy, then the charging procedure is interrupted before the defibrillator is automatically deactivated. Thus, the capacitor 4 does not then have the quantity of energy desired by the operator, but a value which is less than that quantity. This value which is less than the quantity is indicated and made available to the user.

The quantity of residual energy can thus be emitted to a patient; this is advantageous, particularly in circumstances in which the capacitor 4 has for example been charged to 90% of the desired energy before the defibrillator is automatically deactivated. These quantities of energy of 90% of the desired energy may in fact be therapeutically very effective and in particular are available much more speedily than if a change of accumulator or recharging of the accumulator is undertaken beforehand.

In place of an accumulator, it is of course also possible in a similar fashion to use a non-rechargeable battery.

What is claimed is:

1. A defibrillator having a capacitor (4) which is chargeable via a DC-DC converter (3) by an accumulator (1), characterized in that a control device (2) is situated between the accumulator (1) and the capacitor (4) which control device (2)

as the internal resistance (Ri) of the accumulator (1) increases, draws a lower current from the latter, so that the output voltage of the accumulator (1) is kept approximately constant, and interrupts the charging of the capacitor (4) before the defibrillator is automatically deactivated and internally destroys the energy already stored in the capacitor (4) when the residual energy remaining in the accumulator (1) is not sufficient to charge the capacitor (4) to the desired energy, and in that, moreover, the energy already stored in the capacitor (4) is indicated.

2. A defibrillator comprising:

a rechargeable battery having an internal resistance, an output current and an output voltage;

a capacitor; and a controller electrically connected between the rechargeable battery and the capacitor such that as the internal resistance of the rechargeable battery increases, the controller draws less current from the rechargeable battery to approximately maintain a constant rechargeable battery output voltage, and so that, before the defibrillator is automatically deactivated and energy already stored in the capacitor is internally destroyed, the controller interrupts the charging of the capacitor when the residual energy remaining in the rechargeable battery is less than an amount required to charge the capacitor to the desired energy.

3. A defibrillator as set forth in claim 2 wherein the defibrillator includes an external display and wherein the energy stored in the capacitor when the controller interrupts charging of the capacitor is indicated on the external display.

4. A method of controlling a defibrillator, the defibrillator including a rechargeable battery having an internal resistance, an output current, and an output voltage; a capacitor; and a controller electrically connected between the rechargeable battery and the capacitor, the method comprising:

approximately maintaining a constant output voltage of the rechargeable battery in response to an increase in the internal resistance of the rechargeable battery, and interrupting the charging of the capacitor when the residual energy remaining in the rechargeable battery is insufficient to charge the capacitor to a desired energy level.

5. A method of controlling a defibrillator as set forth in claim 4, wherein said act of interrupting the charging of the capacitor is executed before the defibrillator is automatically deactivated thereby destroying the energy already stored in the capacitor.

6. A method of controlling a defibrillator as set forth in claim 4, wherein the defibrillator includes an external display and wherein the method further comprises the act of displaying the energy stored in the capacitor on the external display.

7. A method of controlling a defibrillator as set forth in claim 4 wherein said act of approximately maintaining said constant output voltage of the rechargeable battery in response to an increase in the internal resistance of the rechargeable battery further comprises the acts of monitoring said output voltage and decreasing said output current when said output voltage decreases to a threshold.

\* \* \* \* \*